US010087135B2

(12) United States Patent
Liu et al.

(10) Patent No.: US 10,087,135 B2
(45) Date of Patent: Oct. 2, 2018

(54) LOWER FATTY CARBOXYLIC ACID ALKYL ESTER PRODUCTION METHOD

(71) Applicant: Dalian Institute of Chemical Physics, Chinese Academy of Sciences, Shahekou Dalian (CN)

(72) Inventors: Hongchao Liu, Shahekou Dalian (CN); Wenliang Zhu, Shahekou Dalian (CN); Youming Ni, Shahekou Dalian (CN); Yong Liu, Shahekou Dalian (CN); Zhongmin Liu, Shahekou Dalian (CN); Linying Wang, Shahekou Dalian (CN); Peng Tian, Shahekou Dalian (CN)

(73) Assignee: Dalian Institute of Chemical Physics, Chinese Academy of Sciences, Shahekou, Dalian (CN)

( * ) Notice: Subject to any disclaimer, the term of this patent is extended or adjusted under 35 U.S.C. 154(b) by 0 days.

(21) Appl. No.: 15/743,904

(22) PCT Filed: Dec. 8, 2015

(86) PCT No.: PCT/CN2015/096646
§ 371 (c)(1),
(2) Date: Jan. 11, 2018

(87) PCT Pub. No.: WO2017/012244
PCT Pub. Date: Jan. 26, 2017

(65) Prior Publication Data
US 2018/0201568 A1 Jul. 19, 2018

(30) Foreign Application Priority Data

Jul. 20, 2015 (CN) .......................... 2015 1 0426698

(51) Int. Cl.
| | | |
|---|---|---|
| C07C 67/37 | (2006.01) | |
| B01J 29/08 | (2006.01) | |
| C07C 69/14 | (2006.01) | |
| C07C 69/24 | (2006.01) | |
| C07C 29/17 | (2006.01) | |
| C07C 51/09 | (2006.01) | |

(52) U.S. Cl.
CPC .............. *C07C 67/37* (2013.01); *B01J 29/08* (2013.01); *C07C 29/172* (2013.01); *C07C 51/09* (2013.01); *C07C 69/14* (2013.01); *C07C 69/24* (2013.01)

(58) Field of Classification Search
CPC ........... C07C 67/37; C07C 51/09; B01J 29/08
See application file for complete search history.

(56) References Cited

U.S. PATENT DOCUMENTS

| | | | | |
|---|---|---|---|---|
| 5,218,140 A * | 6/1993 | Wegman | ................... | B01J 23/30 |
| | | | | 554/131 |
| 7,309,798 B2 * | 12/2007 | Cheung | ................... | C07C 51/09 |
| | | | | 560/232 |
| 7,465,822 B2 * | 12/2008 | Cheung | ................... | C07C 51/09 |
| | | | | 560/232 |
| 2007/0238897 A1 * | 10/2007 | Cheung | ................... | C07C 51/09 |
| | | | | 560/232 |
| 2010/0267985 A1 * | 10/2010 | Corma Canos | .......... | B01J 29/20 |
| | | | | 560/232 |

FOREIGN PATENT DOCUMENTS

| | | | | | |
|---|---|---|---|---|---|
| CN | 101613274 | A | | 12/2009 | |
| CN | 101687759 | A | | 3/2010 | |
| CN | 101903325 | A | | 12/2010 | |
| CN | 102950018 | A | | 3/2013 | |
| CN | 103896769 | A | | 7/2014 | |
| DE | 3606169 | | * | 8/1987 | ............. C07C 27/00 |
| WO | WO-2008073096 | A1 | * | 6/2008 | ............. C07C 51/09 |
| WO | 2008/132450 | A1 | | 11/2008 | |
| WO | WO-2008132450 | A1 | * | 11/2008 | ............. C07C 51/09 |
| WO | 2009/081099 | A1 | | 7/2009 | |
| WO | 2010/130972 | A2 | | 11/2010 | |
| WO | WO-2010130972 | A2 | * | 11/2010 | ............. B01J 29/18 |
| WO | WO-2014101901 | A1 | * | 7/2014 | ............. C07C 67/37 |

OTHER PUBLICATIONS

DE 3606169, Caesar F., Process for preparing acetic acid, methyl acetate and/or dimethyl ether, English translation, 1 page (Year: 1987).*

Shikada et al., "Vapor Phase Carbonylation of Dimethyl Ether and Methyl Acetate with Nickel-Active Carbon Catalysts", Applied Catalysis, 1983, pp. 361 to 368, vol. 7, Elsevier Scienc Publishers B.V., Amsterdam, The Netherlands.

Wegman, Richard W., "Vapour Phase Carbonylation of Methanol or Dimethyl Ether with Metal-ion Exchanged Heteropoly Acid Catalysts", J. Chem. Soc., Chem. Commun., 1994, pp. 947 to 948.

Volkova et al., "Heterogeneous catalysts for halide-free carbonylation of dimethyl ether", Catalysis Letters, Jun. 2002, pp. 175 to 179, vol. 80, No. 3-4, Plenum Publishing Corporation.

Cheung et al., "Selective Carbonylation of Dimethyl Ether to Methyl Acetate Catalyzed by Acidic Zeolites", Angew. Chem. Int. Ed., 2006, pp. 1617 to 1620, vol. 45, Wiley-VCH Verlag GmbH & Co. KGaA.

(Continued)

*Primary Examiner* — Yate' K Cutliff
(74) *Attorney, Agent, or Firm* — Edwin A. Sisson, Attorney at Law, LLC; Jeffrey J. Banyas

(57) ABSTRACT

The present invention provides a method for producing a light fatty acid alkyl ester with the formula of $R_1$—COO—$R_2$, and the method comprises a step in which a alkyl ether with formula of $R_1$—O—$R_2$ and a raw gas containing carbon monoxide go through a reactor loaded with a catalyst for carrying out a carbonylation reaction; wherein the catalyst contains an acidic EMT zeolite molecular sieve; wherein $R_1$ and $R_2$ are independently selected from $C_1$-$C_4$ alkyl groups. The present invention has provided a new method for producing light fatty acid alkyl ester. In the method of the present invention, the carbonylation is carried out in the presence of the catalyst containing the acidic EMT zeolite molecular sieve, and the reaction activity is high, and the stability has been significantly improved, meeting the requirement of industrial production.

15 Claims, No Drawings

(56) References Cited

OTHER PUBLICATIONS

Cheung et al., "Site requirements and elementary steps in dimethyl ether carbonylation catalyzed by acidic zeolites", Journal of Catalysis, Oct. 27, 2006, pp. 110 to 123, vol. 245, Elsevier.
Bhan et al., "Specificity of Sites within Eight-Membered Ring Zeolite Channels for Carbonylation of Methyls to Acetyls", J. Am. Chem. Soc., 2007, pp. 4919 to 4924, vol. 129, American Chemical Society.
Donghui, Wang, "Research on application of a Co-crystallization Molecular Sieve Catalyst in the Reaction of DME Carbonylation to MeOAC", Chemical Production and Technology, Apr. 3, 2013, pp. 14 to 18.
Li et al., "Activity enhancement of ZSM-35 in dimethyl ether carbonylation reaction through alkaline modifications", RSC Advances, Jul. 9, 2013, pp. 16549 to 16557, vol. 3, The Royal Society of Chemistry.
Liu et al., "Dimethyl Ether Carbonylation to Methyl Acetate over HZSM-35", Catal. Lett., Jul. 22, 2010, pp. 33 to 37, vol. 139, Springer Sicence+Business Media, LLC.
Gao et al., "Developments of Synthesis and Application of EMT Zeolites", Chemical Production and Technology, Jun. 19, 2012, pp. 46 to 50.

\* cited by examiner

LOWER FATTY CARBOXYLIC ACID ALKYL ESTER PRODUCTION METHOD

PRIORITIES AND CROSS REFERENCES

This Application claims priority from International Application No. PCT/CN2015/096646 filed on 8 Dec. 2015 and Chinese Application No. 201510426698.8 filed on 20 Jul. 2015, the teachings of each of which are incorporated herein by reference in their entirety.

TECHNICAL FIELD

The present invention refers to a method for producing light fatty acid alkyl ester and the derivatives thereof by carbonylation of lower alkyl ethers, and particularly refers to a method for producing methyl acetate and its derivatives by carbonylation of dimethyl ether.

BACKGROUND

Accompanied with the rapid development of the modern industry, the confliction between supplying and demanding of energy has become increasingly acute. China is a major energy consumer and meanwhile a major country of energy shortage with an urgent desire for searching replaceable energy sources. Ethanol is a clean energy source with a good mutual solubility which can be used as blending component added into gasoline, to partially replace gasoline and improve the octane number and the oxygen content of gasoline. It can also promote gasoline burning sufficiently and decrease the emission of carbon monoxide and hydrocarbons in vehicle exhaust. As a partial replacement of vehicle fuel, ethanol may make the vehicle fuel in China more diversified. Currently, in China cereals, especially corns, has mostly been used as a raw material to manufacture fuel ethanol. China has become the third largest country of ethanol producing and consuming, after Brazil and America. However, according to Chinese national condition, there are many unfavorable factors using cereals as raw material to produce ethanol. In the future, non-cereal routes for producing ethanol will be developed preferably in China.

Started with coal resources, producing ethanol via syngas is an important direction to develope coal chemical engineering industry in China with a broad market prospect. It has great strategic meanings and far-reaching impacts on clean utilization of coal resources, relieving the pressure of lacking oil resources and enhancing energy security in our country. Currently, there are mainly two process routes of preparing ethanol from coal, one of which is preparing ethanol from syngas directly. However, a precious metal, rhodium, is needed to serve as the catalyst in this route, so the cost of the catalyst is relatively high. Moreover, the output of rhodium is limited. The other route is preparing ethanol from syngas through hydrogenation of acetic acid, in which acetic acid is preformed by liquid phase methanol carbonylation from the syngas, and then converts to ethanol by hydrogenation. The second route is mature, but the device used in this route needed to be made of special alloy which is anticorrosive, so the cost is high.

Using dimethyl ether as raw material, methyl acetate can be directly synthesized by carbonylation of dimethyl ether, and methyl acetate can be hydrogenated to ethanol. Although the route is still in research stage, it is a brand new route with great application prospect. In 1983, Fujimoto (*Appl Catal* 1983, 7 (3), 361-368) used Ni/Ac as catalyst to carry out a gas-solid phase reaction of dimethyl ether carbonylation. It was discovered that dimethyl ether can react with CO to generate methyl acetate when the molar ratio of CO/DME is in a range from 2.4 to 4, with selectivity in a range from 80% to 92% and the highest yield of 20%. In 1994, Wegman (*J Chem Soc Chem Comm* 1994, (8), 947-948) carried out a dimethyl ether carbonylation reaction using heteropolyacid $RhW_{12}PO_4/SiO_2$ as the catalyst. The yield of methyl acetate was 16% and nearly no other side products were generated. In 2002, Russian researchers, Volkova and her colleagues (*Catalysis Letters* 2002, 80 (3-4), 175-179) used a cesium phosphotungstate modified Rh as catalyst to carry out the carbonylation reaction of dimethyl ether and the reaction rate is an order of magnitude higher than the Wegman's reaction using $RhW_{12}PO_4/SiO_2$ as catalyst.

In 2006, Enrique Iglesia's research group in Berkeley (*Angew. Chem, Int. Ed.* 45(2006) 10, 1617-1620, *J. Catal.* 245 (2007) 110, *J. Am. Chem. Soc.* 129 (2007) 4919) carried out dimethyl ether carbonylation on the molecular sieves with 8 membered ring and 12 membered ring or 10 membered ring, such as Mordenite and Ferrierite. As a result, it was considered that the carbonylation reaction happenes on the B acid active center of 8 membered ring. The selectivity of methyl acetate was quite good, reaching 99%, but the activity of dimethyl ether carbonylation is very low.

American application US2007238897 disclosed that using molecular sieves with 8 membered ring pore structure, such as MOR, FER and OFF, as catalyst for the carbonylation of ethers, the pore size of the 8 membered ring should be larger than 0.25×0.36 nm. Using mordenite as catalyst under the reaction conditions of 165° C. and 1 MPa, a space-time yield of 0.163-MeOAc(g-Cat.h)$^{-1}$ was achieved. WO2008132450A1 (2008) disclosed a MOR catalyst modified by copper and silver, whose performance is obviously better than unmodified MOR catalyst, on reaction conditions of hydrogen atmosphere and temperature ranging from 250° C. to 350° C. WO2009081099A1 disclosed that the carbonylation performance of MOR catalyst with smaller grains is better than MOR catalyst with bigger grains. WO2010130972A2 disclosed an MOR catalyst treated by desilication and dealuminzation, and the activity and the reaction stability of the MOR catalyst can be significantly enhanced by an optimized combination of acid treatment and alkali treatment. Moreover, CN103896769A disclosed a method for preparing methyl acetate by carbonylation of dimethyl ether, in which mordenite and/or ferrierite were used as the catalyst. CN101903325A disclosed a carbonylation process of preparing acetic acid and/or methyl acetate in which the molecular sieves with MOR framework structure were used as the catalyst. CN101687759A disclosed a method for carbonylating methyl ether in which zeolites with MOR, FER, OFF or GME framework structures were used, specifically such as mordenite, ferrierite, offretite and gmelinite. Wang Donghui ("Application of a cocrystallization molecular sieve catalyst in preparing methyl acetate by carbonylation of dimethyl ether", *Chemical Production and Techniques* (2013), No. 3, Vol 20, 14-18) disclosed an application of a cocrystallization molecular sieve catalyst in preparing methyl acetate by carbonylation of dimethyl ether, in which the catalyst was a cocrystallization molecular sieve containing 2 phases of BEA/MOR. And cocrystallization molecular sieve containing 2 phases of EMT/FAU was mentioned in the first paragraph, without being used for carbonylation of dimethyl ether to methyl acetate. CN102950018A disclosed the reaction data of dimethyl ether carbnylation on a cocrystallization molecular sieve of rare earth ZSM-35/MOR. The results show that the activity and stability of cocrystallization molecular sieve was significantly better than ZSM-35 catalyst, and the stability of cocrystallization molecular sieve was significantly better than MOR catalyst. Xu Longya and his colleagues (RSC Adv. 2013, 3:16549-16557) also reported the reaction properties of ZSM-35 treated by alkali in carbonylation of dimethyl ether. The results show that after being treated by alkali, ZSM-35 has an apparent mesoporous structure, enhancing the diffusion effects of reactants and products on the catalyst, and the stability and activity of the catalyst was improved.

In CN101613274A, pyridine organic amines were used to modify mordenite molecular sieve catalyst, and it was discovered that the modification of molecular sieve can dramatically enhance the stability of catalyst. The percent conversion of dimethyl ether was in a range from 10% to 60%, and the selectivity of methyl acetate was over 99%. Moreover, the activity of the catalyst remained stable after reacting for 48 h. Shen Wenjie (Catal. Lett. 2010, 139:33-37) and his colleagues made a research on preparing methyl acetate by carbonylation of dimethyl ether, comparing the reaction activity on MOR and ZSM-35 catalyst. It was discovered that ZSM-35 molecular sieve has better reaction stability and products selectivity, and under the reaction conditions of 250 □, 1 MPa, DME/CO/N$_2$/He=5/50/2.5/42.5 and 12.5 mL/min, the percent conversion of dimethyl ether could reach 11%, and the selectivity of methyl acetate could reach 96%.

The above references has disclosed a lot of research results on dimethyl ether carbonylation, and research on the catalyst has mainly focused on MOR, FER, and the like with a structure of 8 membered ring. In the results reported publicly, those catalysts are very easy to become inactivated with catalyst life of less than 100 h. And additionally, the reaction results cannot meet the requirement of industrial production.

SUMMARY OF THE INVENTION

The purpose of the present invention is to provide a new method for producing light fatty acid alkyl ester.

The inventors of the present invention found that the carbonylation reaction of low alkyl ether is a typical acid catalyzed reaction, and the acidity and pore structure of the catalyst have a decisive influence on the catalytic performance of the catalyst. EMT zeolite belongs to the hexagonal system, the space group of P$_{63}$/mmc with the cell parameters of a=b=1.7374 nm and c=2.8365 nm, and the framework density of 12.9 T/nm$^3$. Its framework structure is a simple hexagonal analogue of faujasite zeolite FAU, composed of 12 membered rings, 6 membered rings and 4 membered rings. As a zeolite with a better topology structure than FAU, it has a stronger acidity and a bigger acid quantity. At the same time, EMT has two sets of intersecting cavities which are connected by 2 dimensional cross channels. Its superior pore connectivity is more conducive to the adsorption of reactants and the diffusion of product molecules.

Therefore, the present invention provides a method for producing fatty acid alkyl ester with formula of R$_1$—COO—R$_2$, which comprises a step carrying out a carbonylation reaction of a alkyl ether with formula of R$_1$—O—R$_2$ and a raw gas containing carbon monoxide in the presence of a catalyst containing an acidic EMT zeolite molecular sieve; wherein R$_1$ and R$_2$ are independently selected from C$_1$-C$_4$ alkyl groups. Preferably, the R$_1$ and the R$_2$ are independently selected from CH$_3$—, CH$_3$CH$_2$—, CH$_3$(CH$_2$)$_2$—, (CH$_3$)$_2$CH—, CH$_3$(CH$_2$)$_3$— or (CH$_3$)$_3$CH—. More preferably, both of the R$_1$ and the R$_2$ are CH$_3$—.

In a preferred embodiment, the molar ratio of silicon atoms to aluminum atoms in the acidic EMT zeolite molecular sieve is in a range from 1.5 to 30. Preferably, the molar ratio of silicon atoms to aluminum atoms in the acidic EMT zeolite molecular sieve is in a range from 2 to 15.

In a preferred embodiment, the acidic EMT zeolite molecular sieve contains a catalyst promoter which is one or more metals selected from gallium, iron, copper and silver. Preferably, the catalyst promoter is introduced to the acidic EMT zeolite molecular sieve by a method selected from in-situ synthesis, metal ion exchange or impregnation loading. More preferably, based on the total weight of the catalyst, the weight fraction of the catalyst promoter calculated by weight of metal elementary substance is in a range from 0.01 wt % to 10 wt %.

In a preferred embodiment, the acidic EMT zeolite molecular sieve contains a binder which is one or more compounds selected from alumina, silicon dioxide and magnesium oxide. Preferably, based on the total weight of the catalyst, the weight fraction of the binder is in a range from 0 wt % to 50 wt %.

In a preferred embodiment, the fatty acid alkyl ester is further hydrolyzed to a corresponding carboxylic acid. Preferably, the corresponding carboxylic acid is acetic acid.

In a preferred embodiment, the fatty acid alkyl ester is further hydrogenated to a corresponding alcohol. Preferably, the corresponding alcohol is ethyl alcohol.

In a preferred embodiment, the raw gas containing carbon monoxide contains carbon monoxide, hydrogen and one or more inactive gases selected from nitrogen, helium, argon, carbon dioxide, methane and ethane. Preferably, based on the total volume of the raw gas containing carbon monoxide, the volume fraction of carbon monoxide is in a range from 50% to 100%, and the volume fraction of hydrogen is in a range from 0% to 50%, and the volume fraction of the inert gas is in a range from 0% to 50%.

In a preferred embodiment, the carbonylation reaction is carried out at a temperature range from 170 □ to 240 □ and at a pressure range from 1 MPa to 15 MPa.

In a preferred embodiment, the carbonylation reaction is carried out in a fixed bed reactor, a fluidized bed reactor or a moving bed reactor.

The present invention provides a new method for producing light fatty acid alkyl esters, especially a new method for producing methyl acetate. In the method of the present invention, the carbonylation is carried out in the presence of the catalyst containing the acidic EMT zeolite molecular sieve, and the reaction activity is high, and the stability has been significantly improved, meeting the requirement of industrial production.

DETAILED DESCRIPTION OF THE EMBODIMENT

The present invention provides a method for synthesizing fatty acid alkyl ester with formula of R$_1$—COO—R$_2$, which comprises a step carrying out a carbonylation reaction of an alkyl ether with formula of R$_1$—O—R$_2$ and a raw gas containing carbon monoxide on a catalyst containing an acidic EMT zeolite molecular sieve. Preferably, the carbonylation reaction is carried out under the conditions without water or with trace water. R$_1$ and R$_2$ are independently selected from C$_1$-C$_4$ alkyl groups, such as CH$_3$—, CH$_3$CH$_2$—, CH$_3$(CH$_2$)$_2$—, (CH$_3$)$_2$CH—, CH$_3$(CH$_2$)$_3$— or (CH$_3$)$_3$CH—.

In the present invention, the term 'light fatty acid alkyl ester' refers to the fatty acid alkyl ester expressed in formula of $R_1$—COO—$R_2$, wherein $R_1$ and $R_2$ are independently selected from $C_1$-$C_4$ alkyl groups.

In a particular embodiment, the present invention provides a method for producing methyl acetate by carbonylation reaction of dimethyl ether and carbon monoxide on an acidic zeolite molecular sieve catalyst with EMT topological structure.

Preferably, the molar ratio of silicon atoms to aluminum atoms in the acidic EMT zeolite molecular sieve used in the present invention is in a range from 1.5 to 30. Preferably, the molar ratio of silicon atoms to aluminum atoms in the acidic EMT zeolite molecular sieve of the present invention is in a range from 2 to 15.

Preferably, the acidic EMT zeolite molecular sieve used in the present invention contains a catalyst promoter which is one or more metals selected from gallium, iron, copper and silver (which may exist in the form of metal elementary substance or metal compounds such as metal oxides). For instance, the catalyst promoter is introduced to the acidic EMT zeolite molecular sieve by a method selected from in-situ synthesis, metal ion exchange or impregnation loading. Preferably, based on the total weight of the catalyst, the weight fraction of the catalyst promoter calculated by weight of metal elementary substance is in a range from 0.01 wt % to 10 wt %.

Preferably, the acidic EMT molecular sieve used in the present invention contains a binder which is one or more compounds selected from alumina, silicon dioxide and magnesium oxide. Preferably, the weight fraction of the binder in the total weight of the catalyst is in a range from 0 wt % to 50 wt %.

Preferably, the raw gas containing carbon monoxide used in the present invention contains carbon monoxide, hydrogen and one or more inactive gases selected from nitrogen, helium, argon, carbon dioxide, methane and ethane. Preferably, based on the total volume of the raw gas containing carbon monoxide, the volume fraction of carbon monoxide is in a range from 50% to 100%, and the volume fraction of hydrogen is in a range from 0% to 50%, and the volume fraction of the inert gas is in a range from 0% to 50%.

Preferably, the alkyl ether used in the present invention is dimethyl ether, and the fatty acid alkyl ester obtained after carbonylation is methyl acetate.

Preferably, the fatty acid alkyl ester synthesized by the method of the present invention can be further hydrolyzed to a corresponding carboxylic acid. For instance, the methyl acetate obtained above can be used to produce acetic acid.

Preferably, the raw gas containing carbon monoxide used in the present invention can also contain hydrogen and an inactive gas. The inactive gas can be one or more inactive gases selected from nitrogen, helium, argon, carbon dioxide, methane and ethane.

Preferably, the carbonylation reaction in the present invention is carried out at a temperature range from 170 □ to 240 □ and at a pressure range from 1 MPa to 15 MPa.

Preferably, the carbonylation reaction in the present invention is carried out in a fixed bed reactor, a fluidized bed reactor or a moving bed reactor.

In addition, although no special restrictions are required, the molar ratio of dimethyl ether and carbon monoxide is preferably in a range from 1:20 to 1:0.5 in a preferred carbonylation reaction.

EXAMPLES

The present invention will be described in details by Examples, but the present invention is not limited to these Examples.

In the examples, the calculation of percent conversion of alkyl ether (represented by dimethyl ether) and selectivity of light fatty acid alkyl ester (represented by methyl acetate) was based on the carbon mole number:

Percent conversion of dimethyl ether=[(the carbon mole number of dimethyl ether in the feed gas)−(the carbon mole number of dimethyl ether in the product)]÷(the carbon mole number of dimethyl ether in the feed gas)×(100%)

Selectivity of methyl acetate=(⅔)×(the carbon mole number of methyl acetate in the product)÷[(the carbon mole number of dimethyl ether in the feed gas)−(the carbon mole number of dimethyl ether in the product)]×(100%)

Four samples of Na-EMT zeolite molecular sieve whose molar ratios of silicon atom to aluminum atom respectively are 2, 4, 15 and 25, a sample of Na-EMT zeolite molecular sieve containing Ga whose molar ratio of silicon atom to aluminum is 4, and a sample of Na-EMT zeolite molecular sieve containing Fe whose molar ratio of silicon atom to aluminum is 4 have been used in the Examples. All of them were produced and provided by Dalian Institute of Chemical Physics.

Examples for Preparing the Catalyst

H-EMT Catalyst 100 g of a sample of Na-EMT zeolite molecular sieve was exchanged with 0.5 mol/L of ammonium nitrate for three times and each time was for 2 hours. And then the solid product was washed with deionized water, dried, calcined at 550° C. for 4 h, pressed, crushed and sieved to 20-40 mesh used as the catalyst sample. Four samples of Na-EMT zeolite molecular sieve with molar ratios of silicon atom to aluminum atom of 2, 4, 15 and 25 were used, to obtain the samples of Catalyst 1#, Catalyst 2#, Catalyst 3# and Catalyst 4#, respectively.

Ga-EMT Catalyst 100 g of the sample of Na-EMT zeolite molecular sieve containing Ga (the molecular ratio of silicon atom to aluminum is 4) was exchanged with 0.5 mol/L of ammonium nitrate for three times and each time was for 2 hours. And then the solid product was washed with deionized water, dried, calcined at 550° C. for 4 h, pressed, crushed and sieved to 20-40 mesh to obtain the sample of Catalyst 5#.

Fe-EMT Catalyst 100 g of the sample of Na-EMT zeolite molecular sieve containing Fe (the molecular ratio of silicon atom to aluminum is 4) was exchanged with 0.5 mol/L of ammonium nitrate for three times and each time was for 2 hours. And then the solid product was washed with deionized water, dried, calcined at 550° C. for 4 h, pressed, crushed and sieved to 20-40 mesh to obtain the sample of Catalyst 6#.

Supported Catalyst of M/EMT

The supported catalyst of M/EMT was prepared using equivalent-volume impregnation method. 4.32 g of $Fe(NO_3)_3$, 4.32 g of $Cu(NO_3)_2.3H_2O$ and 3.04 g of $AgNO_3.3H_2O$ were respectively dissolved in 18 mL of deionized water to form the $Fe(NO_3)_3$ aqueous solution, $Cu(NO_3)_2$ aqueous solution and $AgNO_3$ aqueous solution. 20 g of Catalyst 2# (H-EMT zeolite molecular sieve catalyst) was added into the $Fe(NO_3)_3$ aqueous solution, $Cu(NO_3)_2$ aqueous solution and $AgNO_3$ aqueous solution, respectively. After standing for 24 hours, the solid products were separated, washed by deionized water, dried in the oven at 120 □ for 12 hours, and then the samples obtained were put into a muffle furnace whose temperature was heated to 550 □ at a heating rate of 2° C./min, calcined at 550° C. in air for 4 h to obtain the samples of Catalyst 7#, Catalyst 8# and Catalyst 9#.

Ion Exchange Catalyst of M-EMT 20 g of Catalyst 2# (H-EMT zeolite molecular sieve catalyst) and 300 mL of 0.15 mol ferric nitrate aqueous solution were placed in a flask, being stirred for 2 hours at 80° C. under the condition of cooling and refluxing with solid-liquid ratio of 1:15. The solid product was separated by filtration and washed by deionized water. Repeating the above steps for 2 times, the sample obtained was dried at 120° C. for 12 hours, and the dried sample was put into a muffle furnace whose temperature was heated to 550° C. at a heating rate of 2° C./min, calcined at 550° C. in air for 4 h to obtain the sample of Catalyst 10#.

Molded Catalyst of H-EMT 80 g of Na-EMT zeolite molecular sieve with molar ratio of silicon atom to aluminum of 4, 28 g of pseudo-boehmite and 10% of diluted nitric acid were uniformly mixed, and then the mixture was molded through extrusion. After being calcined at 550° C. for 4 hours, the molded sample was exchanged with 0.5 mol/L of ammonium nitrate for three times (2 hours/time). And then the solid product was washed by deionized water, dried, calcined at 550° C. for 4 h to obtain the sample of Catalyst 11#.

80 g of Na-EMT zeolite molecular sieve with molar ratio of silicon atom to aluminum of 4, 20 g of magnesium oxide and 10% of diluted nitric acid were uniformly mixed, and then the mixture was molded through extrusion. After being calcined at 550° C. for 4 hours, the molded sample was exchanged with 0.5 mol/L of ammonium nitrate for three times and each time was for 2 hours. And then the solid product was washed by deionized water, dried, calcined at 550° C. for 4 h to obtain the sample of Catalyst 12#.

80 g of Na-EMT zeolite molecular sieve with molar ratio of silicon atom to aluminum of 4, 50 g of silicon sol and 10% of diluted nitric acid were uniformly mixed, and then the mixture was molded through extrusion. After being calcined at 550° C. for 4 hours, the molded sample was exchanged with 0.5 mol/L of ammonium nitrate for three times (2 hours/time). And then the solid product was washed by deionized water, dried, calcined at 550° C. for 4 h to obtain the sample of Catalyst 13#.

Examples of Synthesis

Comparative Example

H-MOR (molar ratio of silicon atom to aluminum atom Si/Al=6.7) was used as a comparative catalyst. 10 g of the comparative catalyst was put into a tubular fixed bed reactor with inner diameter of 28 mm, and then was heated to 550° C. at a heating rate of 5° C./min under nitrogen gas. After being kept at 550° C. for 4 hours, the temperature was reduced to the reaction temperature of 190° C. in nitrogen gas, and then the pressure was increased to the reaction pressure of 5 MPa by introducing CO. The space velocity of feeding dimethyl ether was 0.10 $h^{-1}$, and the molar ratio of dimethyl ether to carbon monoxide was 1:6, and the molar ratio of carbon monoxide to hydrogen in the raw gas containing carbon monoxide was 2:1. The results at the time on stream (TOS) of 1 h, 50 h and 100 h, are shown in Table 1.

TABLE 1

Results of the comparative catalyst

| Time on stream (h) | 1 | 50 | 100 |
|---|---|---|---|
| Percent conversion of dimethyl ether (%) | 35.7 | 23.8 | 9.8 |
| Selectivity of methyl acetate (%) | 99.8 | 78.2 | 25.3 |

Example 1

According to Table 2, 10 g of the catalyst was put into a tubular fixed bed reactor with inner diameter of 28 mm, and then was heated to 550° C. at a heating rate of 5° C./min under nitrogen gas. After being kept at 550° C. for 4 hours, the temperature was reduced to the reaction temperature of 190° C. in nitrogen gas, and then the pressure was increased to the reaction pressure of 5 MPa by introducing CO. The space velocity of feeding dimethyl ether was 0.10 $h^{-1}$, and the molar ratio of dimethyl ether to carbon monoxide was 1:6, and the molar ratio of carbon monoxide to hydrogen in the raw gas containing carbon monoxide was 2:1. The results are shown in Table 2.

TABLE 2

Evaluation results of catalyst for dimethyl ether carbonylation

| | TOS = 1 h | | TOS = 50 h | | TOS = 100 h | |
|---|---|---|---|---|---|---|
| Catalyst | Percent conversion of dimethyl ether (%) | Selectivity of methyl acetate (%) | Percent conversion of dimethyl ether (%) | Selectivity of methyl acetate (%) | Percent conversion of dimethyl ether (%) | Selectivity of methyl acetate (%) |
| 1# | 8.1 | 99.8 | 7.9 | 99.2 | 7.5 | 95.3 |
| 2# | 22.1 | 99.7 | 21.3 | 99.2 | 17.5 | 95.3 |
| 3# | 34.7 | 99.6 | 31.8 | 98.3 | 23.5 | 97.7 |
| 4# | 29.1 | 99.1 | 28.9 | 98.2 | 24.5 | 96.3 |
| 5# | 30.7 | 98.3 | 29.8 | 97.3 | 27.5 | 91.6 |
| 6# | 32.7 | 98.3 | 32.8 | 97.3 | 31.5 | 91.6 |
| 7# | 27.7 | 98.3 | 26.8 | 97.3 | 24.5 | 91.6 |
| 8# | 28.3 | 98.3 | 27.8 | 97.3 | 25.3 | 91.6 |
| 9# | 28.2 | 98.3 | 27.3 | 97.3 | 24.2 | 91.6 |
| 10# | 30.7 | 98.3 | 29.8 | 97.3 | 26.8 | 91.6 |
| 11# | 19.1 | 99.9 | 18.3 | 99.2 | 17.5 | 98.3 |
| 12# | 17.1 | 99.1 | 16.3 | 98.7 | 15.5 | 97.3 |
| 13# | 15.1 | 99.3 | 14.3 | 98.2 | 14.2 | 97.3 |

TOS: Time on stream

Example 2

Reaction results of dimethyl ether carbonylation at different reaction temperatures 10 g of Catalyst 3# was put into a tubular fixed bed reactor with inner diameter of 28 mm, and then was heated to 550 °C at a heating rate of 50/min under nitrogen gas. After being kept at 550 °C for 4 hours, the temperature was reduced to the reaction temperature in nitrogen gas, and then the pressure was increased to the reaction pressure of 5 MPa by introducing CO. The raw material went through the catalyst bed from top to bottom. The space velocity of feeding dimethyl ether was 0.10 h$^{-1}$, and the molar ratio of carbon monoxide to dimethyl ether was 6:1, and the molar ratio of carbon monoxide to hydrogen in the raw gas containing carbon monoxide was 2:1. The results at the reaction time when the catalytic reaction ran on for 100 h are shown in Table 3.

TABLE 3

Reaction results of dimethyl ether on H-EMT catalyst at different reaction temperatures

| Reaction temperature (°C) | 170 | 200 | 230 | 240 |
|---|---|---|---|---|
| Percent conversion of dimethyl ether (%) | 15.7 | 42.1 | 76.0 | 87.8 |
| Selectivity of methyl acetate (%) | 97.8 | 99.7 | 94.5 | 90.4 |

Example 3

Reaction Results of Dimethyl Ether Carbonylation at Different Reaction Pressures The Catalyst 4# was used. The reaction pressures were 1 MPa, 6 MPa, 10 MPa and 15 MPa, respectively, and other experimental conditions were same as Example 1. The results at the reaction time when the catalytic reaction ran on for 100 h are shown in Table 4.

TABLE 4

Reaction results of dimethyl ether on H-EMT catalyst at different reaction pressures

| Reaction pressure (MPa) | 1 | 6 | 10 | 15 |
|---|---|---|---|---|
| Percent conversion of dimethyl ether (%) | 18.3 | 29.3 | 41.8 | 52.3 |
| Selectivity of methyl acetate (%) | 98.7 | 99.1 | 99.4 | 99.8 |

Example 4

Reaction Results of Dimethyl Ether Carbonylation at Different Space Velocities of Dimethyl Ether The Catalyst 6# was used. The space velocities of dimethyl ether were 0.25 h$^{-1}$, 1 h$^{-1}$ and 2h$^{-1}$, respectively, and other experimental conditions were same as Example 1. The results at the reaction time when the catalytic reaction ran on for 100 h are shown in Table 5.

TABLE 5

Reaction results of dimethyl ether on H-EMT catalyst at different space velocities of dimethyl ether

| Space velocity of dimethyl ether (h$^{-1}$) | 0.25 | 1 | 2 |
|---|---|---|---|
| Percent conversion of dimethyl ether (%) | 18.3 | 14.3 | 10.8 |
| Selectivity of methyl acetate (%) | 99.7 | 99.1 | 97.9 |

Example 5

Reaction Results of Dimethyl Ether Carbonylation Under Different Molar Ratio of Dimethyl Ether to Carbon Monoxide The Catalyst 6# was used. The molar ratios of carbon monoxide to dimethyl ether were 12:1, 8:1, 4:1 and 2:1, respectively, and other experimental conditions were same as Example 1. The results at the reaction time when the catalytic reaction ran on for 100 h are shown in Table 6.

TABLE 6

Reaction results of dimethyl ether on H-EMT catalyst under different molar ratio of dimethyl ether to carbon monoxide

| Mole ratio of carbon monoxide/dimethyl ether | 1:12 | 1:8 | 1:4 | 1:2 |
|---|---|---|---|---|
| Percent conversion of dimethyl ether (%) | 43.6 | 36.7 | 18.8 | 12.3 |
| Selectivity of methyl acetate (%) | 97.8 | 98.1 | 99.5 | 99.4 |

Example 6

Reaction Results of Dimethyl Ether Carbonylation when the Raw Gas Containing Carbon Monoxide Also Contains an Inactive Gas The Catalyst 9# was used. The space velocities of dimethyl ether was 0.1 h$^{-1}$, and the molar ratio of dimethyl ether to carbon monoxide was 1:9, and the reaction temperature was 190 °C, and other experimental conditions were same as Example 1. The results at the reaction time when the catalytic reaction ran on for 200 h are shown in Table 7.

TABLE 7

Reaction results of dimethyl ether on H-EMT catalyst when the raw gas containing carbon monoxide also contains an inactive gas

| Volume fraction of inert gas | Volume fraction of CO | Percent conversion of dimethyl ether (%) | Selectivity of methyl acetate (%) |
|---|---|---|---|
| 1% (H$_2$) | 99% | 33.5 | 96.8 |
| 48% (H$_2$) | 52% | 13.9 | 97.8 |
| 1% (N$_2$) | 99% | 33.5 | 96.5 |
| 48% (N$_2$) | 52% | 12.6 | 95.2 |
| 20% (N$_2$) + 28% (H$_2$) | 52% | 13.1 | 96.7 |
| 20% (CO$_2$) + 28% (H$_2$) | 52% | 13.2 | 96.7 |

Example 7

Reaction Results in Different Type of Reactors

The Catalyst 2# was used. The reaction temperature was 230 °C, and the reactors were a fluidized bed reactor and a moving bed reactor, respectively, and other experimental conditions were same as Example 1. The reaction results are shown in Table 8.

TABLE 8

Reaction results on H-EMT catalyst in different type of reactors

| Type of reactor | fluidized bed | moving bed |
|---|---|---|
| Percent conversion of of dimethyl ether (%) | 89.2 | 91.5 |
| Selectivity of methyl acetate (%) | 98.7 | 98.5 |

Example 8

Reaction Results on H-EMT Catalyst when the Alkyl Ether is not Dimethyl Ether

The $R_1$ and $R_2$ were same group and both were not methyl, and other experimental conditions were same as Example 1. The reaction results are shown in Table 9.

TABLE 9

Reaction results on H-EMT catalyst when the alkyl ether is not dimethyl ether

| $R_1$ | $R_2$ | Percent conversion of $R_1$—O—$R_2$ (%) | Selectivity of R—COO—R (%) |
|---|---|---|---|
| $CH_3CH_2$— | $CH_3CH_2$— | 30.6 | 98.2 |
| $CH_3(CH_2)_2$— | $CH_3(CH_2)_2$— | 28.7 | 97.8 |
| $(CH_3)_3CH$— | $(CH_3)_3CH$— | 26.8 | 98.8 |

Example 9

Methyl Acetate Hydrolysis to Acetic Acid

The carbonylation product methyl acetate was hydrolyzed to acetic acid in the presence of hydrolyzing catalyst. The ratio of water to ester was 4, and space velocity of methyl acetate was 0.4 $h^{-1}$, and loading amount of the catalyst was 10 g. The reaction results are shown in Table 10.

TABLE 10

Reaction result of methyl acetate hydrolysis to acetic acid

| Reaction temperature (□) | 50 | 60 | 70 |
|---|---|---|---|
| Percent conversion of methyl acetate (%) | 55.7 | 72.1 | 89.0 |

Example 10

Methyl Acetate Hydrogenation to Ethanol

The carbonylation product methyl acetate was hydrogenated to ethanol in the presence of hydrogenation catalyst. The reaction pressure was 5.5 MPa, and the molar ratio of hydrogen tp methyl acetate in raw gas was 20:1, and the molar ratio of hydrogen to carbon monoxide was 20:1, and the space velocity of methyl acetate was 3 $h^{-1}$, and loading amount of the catalyst was 10 g. The reaction results are shown in Table 11.

TABLE 11

Reaction results of methyl acetate hydrogenation to ethanol

| | Methyl acetate hydrogenation | | |
|---|---|---|---|
| Reaction temperature (□) | Percent conversion of methyl acetate (%) | Selectivity of Ethanol (%) | Selectivity of Methanol (%) |
| 180 | 68.1 | 39.7 | 53.2 |
| 200 | 77.4 | 41.0 | 51.8 |
| 220 | 88.3 | 43.3 | 50.1 |
| 240 | 96.2 | 45.2 | 50.3 |

The present invention has been described in detail as above, but the invention is not limited to the detailed embodiments described in this text. Those skilled in the art will understand that other changes and deformations can be made without deviating from the scope of the invention. The scope of the invention is limited by the appended claims.

The invention claimed is:

1. A method for producing fatty acid alkyl ester with formula of $R_1$—COO—$R_2$, which comprises a step in which an alkyl ether with formula of $R_1$—O—$R_2$ and a raw gas containing carbon monoxide go through a reactor loaded with a catalyst for carrying out a carbonylation reaction; wherein the catalyst contains an acidic EMT zeolite molecular sieve; wherein $R_1$ and $R_2$ are independently selected from $C_1$-$C_4$ alkyl groups.

2. A method for producing fatty acid alkyl ester with formula of $R_1$—COO—$R_2$ according to claim 1, wherein in the acidic EMT zeolite molecular sieve, the molar ratio of silicon atoms to aluminum atoms is in a range from 1.5 to 30.

3. A method for producing fatty acid alkyl ester with formula of $R_1$—COO—$R_2$ according to claim 1, wherein the acidic EMT zeolite molecular sieve contains a catalyst promoter which is one or more metals selected from gallium, iron, copper and silver.

4. A method for producing fatty acid alkyl ester with formula of $R_1$—COO—$R_2$ according to any of claims 1 to 3, wherein the acidic EMT zeolite molecular sieve contains a binder which is one or more compounds selected from alumina, silicon dioxide and magnesium oxide.

5. A method for producing fatty acid alkyl ester with formula of $R_1$—COO—$R_2$ according to claim 1, wherein the $R_1$ and the $R_2$ are independently selected from $CH_3$, $CH_3CH_2$, $CH_3(CH_2)_2$, $(CH_3)_2CH$, $CH_3(CH_2)_3$ or $(CH_3)_3CH$.

6. A method for producing fatty acid alkyl ester with formula of $R_1$—COO—$R_2$ according to claim 1, wherein the fatty acid alkyl ester is hydrolyzed to a corresponding carboxylic acid.

7. A method for producing fatty acid alkyl ester with formula of $R_1$—COO—$R_2$ according to claim 1, wherein the fatty acid alkyl ester is hydrogenated to a corresponding alcohol.

8. A method for producing fatty acid alkyl ester with formula of $R_1$—COO—$R_2$ according to claim 1, wherein the raw gas containing carbon monoxide contains carbon monoxide, hydrogen and one or more inactive gases selected from nitrogen, helium, argon, carbon dioxide, methane and ethane.

9. A method for producing fatty acid alkyl ester with formula of $R_1$—COO—$R_2$ according to claim 1, wherein the carbonylation reaction is carried out at a temperature range from 170° C. to 240° C. and at a pressure range from 1 MPa to 15 MPa.

10. A method for producing fatty acid alkyl ester with formula of $R_1$—COO—$R_2$ according to claim 1, wherein the carbonylation reaction is carried out in a fixed bed reactor, a fluidized bed reactor or a moving bed reactor.

11. A method for producing fatty acid alkyl ester with formula of $R_1$—COO—$R_2$ according to claim 1, wherein in the acidic EMT zeolite molecular sieve, the molar ratio of silicon atoms to aluminum atoms is in a range from 2 to 15.

12. A method for producing fatty acid alkyl ester with formula of $R_1$—COO—$R_2$ according to claim 3, wherein the catalyst promoter is introduced to the acidic EMT zeolite molecular sieve by a method selected from in-situ synthesis, metal ion exchange or impregnation loading.

13. A method for producing fatty acid alkyl ester with formula of $R_1$—COO—$R_2$ according to claim 3, wherein based on the total weight of the catalyst, the weight fraction of the catalyst promoter calculated by weight of metal elementary substance is in a range from 0.01 wt % to 10 wt %.

14. A method for producing fatty acid alkyl ester with formula of $R_1$—COO—$R_2$ according to claim 4, wherein based on the total weight of the catalyst, the weight fraction of the binder is in a range from 0 wt % to 50 wt %.

15. A method for producing fatty acid alkyl ester with formula of $R_1$—COO—$R_2$ according to claim 8, wherein based on the total volume of the raw gas containing carbon monoxide, the volume fraction of carbon monoxide is in a range from 50% to 100%, and the volume fraction of hydrogen is in a range from 0% to 50%, and the volume fraction of the inert gas is in a range from 0% to 50%.

* * * * *